United States Patent [19]

Cox et al.

[11] Patent Number: 4,638,816
[45] Date of Patent: Jan. 27, 1987

[54] SMOKING COMPOSITIONS CONTAINING A GLYCOSYLAMINE FLAVORANT ADDITIVE

[75] Inventors: Richard H. Cox, Midlothian; Harvey J. Grubbs, Mechanicsville; Stephen A. Haut, Chesterfield, all of Va.

[73] Assignee: Philip Morris Incorporated, New York, N.Y.

[21] Appl. No.: 714,774

[22] Filed: Mar. 22, 1985

[51] Int. Cl.$^4$ ................................................ A24B 3/12
[52] U.S. Cl. .................................................... 131/276
[58] Field of Search ................................. 131/276, 275

Primary Examiner—V. Millin

[57] ABSTRACT

This invention provides smoking compositions which contain a glycosylamine compound as a flavorant-release additive. Under cigarette smoking conditions, an additive such as 1-amino-1-deoxyglucose pyrolyzes into volatile constituents which enhance the flavor of the mainstream smoke and the aroma of sidestream smoke.

15 Claims, No Drawings

SMOKING COMPOSITIONS CONTAINING A GLYCOSYLAMINE FLAVORANT ADDITIVE

BACKGROUND OF THE INVENTION

It is well known in the tobacco art that the flavor and aroma of the smoke from the tobacco are very important considerations insofar as the ultimate consumer is concerned. There is extensive commitment by the manufacturers of smoking compositions to provide products that are acceptable to the consumer, particularly with respect to flavor and aroma characteristics. It has been the common practice in the tobacco industry to prepare blends of domestic and oriental tobaccos in order to provide smoking compositions which have a pleasing flavor and aroma during smoking. However, such blending is a costly practice and it is subject to the vagaries of tobacco filler supplies. In particular, burley tobacco is an advantageous component of smoking tobacco blends but it is of increasingly scarce supply and high cost.

As an alternative means of providing smoking compositions with desirable flavor characteristics, a variety of flavorants have been developed and proposed for incorporation into tobacco products. Illustrative of such tobacco flavorants are those described in U.S. Pat. Nos. 3,580,259; 3,625,224; 3,722,516; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 4,379,754; and the like.

U.S. Pat. No. 4,036,237 describes smoking compositions which contain an aromatic beta-hydroxy ester flavorant such as ethyl 2,2-dimethyl-3-hydroxy-3-phenylpropionate, which volatilizes under smoking conditions.

U.S. Pat. No. 4,312,368 describes smoking compositions which contain a heterocyclic-hydroxy-substituted carboxylate flavorant-release additive such as ethyl 2-(2-butyl-3-hydroxy-3-methyl-3-(3-pyridyl)propionate. Under smoking conditions this additive pyrolyzes into 3-acetylpyridine and ethyl $\beta$-methylvalerate flavorants.

J. C. Leffingwell et al "Tobacco Flavoring For Smoking Products" (R. J. Reynolds publication, 1972) includes a listing of desirable flavorants for smoking compositions.

Of more specific interest with respect to the present invention subject matter is the proposed utilization of substantially non-volatile reaction products of sugars with aminoacids as tobacco flavorants.

U.S. Pat. No. 3,478,015 describes "browning reactions" in which an amino acid and a sugar having an active carbonyl are reacted in a lower alkyl polyhydric alcohol solvent in the absence of water at a temperature less than 90° C. for about 5-15 hours. The resultant reaction mixture is applied in an amount of about one percent by weight to tobacco as a flavorant additive.

U.S. Pat. No. 3,920,026 describes tobacco flavorants prepared by reacting valine with a carbonyl compound selected from sugars, dihydroxyacetone, or pyruvaldehyde. The reaction is conducted in a solvent such as glycerol or propylene glycol at a temperature between about 120°-200° C. for a period of 0.5-5 hours. The reaction mixture is applied directly onto tobacco, or it is separated into volatile and nonvolatile fractions which respectively are useful as tobacco flavorants.

U.S. Pat. No. 3,722,516 describes the addition of dihydroxyacetone alone or in combination with aminoacids to enhance the natural flavor characteristics of tobacco filler, such as the caramel-like or burned sugar-like flavor and aroma of the tobacco under smoking conditions.

Japanese Pat. No. 9239/71 discloses the use of sugar-aminoacid condensation products as tobacco "perfumes". The condensation product is produced by reacting an aminoacid with a sugar in an aqueous or alcohol solvent, and usually in the presence of an acid catalyst such as malonic acid. The desired compounds can be separated and purified by use of ion-exchange resins and thereafter applied to tobacco filler.

Japanese Pat. No. 3398/73 discloses certain other specific aminoacid-sugars that are synthesized from their respective components by the Amadori rearrangement, by heating at 130° C. for fifteen minutes in the presence of a malic acid catalyst. The specific compounds are isolated, and can be combined with other ingredients such as cocoa to produce tobacco flavorants.

U.S. Pat. No. 4,306,577 describes the preparation of tobacco flavorant compositions by the reaction of a reducing sugar with an aminoacid in the presence of ammonium hydroxide. The reaction product is applied to tobacco filler in an amount between about 0.001-3.0% by weight of the filler blend. The primary effect of the addition of the reaction product to the tobacco is to overcome or alter the "stemmy" taste frequently associated with reconstituted tobacco products.

There is continuing research effort to develop improved smoking compositions which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking tobacco compositions having incorporated therein a flavorant-release additive which under normal smoking conditions imparts improved flavor to mainstream smoke and improved aroma to sidestream smoke.

It is a further object of this invention to provide sugar derivatives which are adapted to be incorporated into cigarette fillers, and which under normal smoking conditions release volatile flavorant constituents into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.001 and 5 weight percent, based on the total weight of filler, of a glycosylamine flavorant-release additive corresponding to the formula:

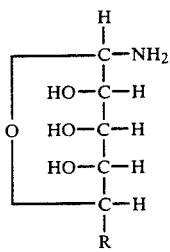

where R is a hydrogen, methyl or methylol substituent.

Illustrative of the invention glycosylamine flavorant compounds is 1-amino-1-deoxyglucose:

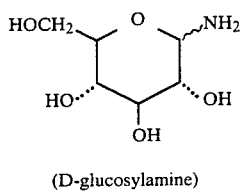

(D-glucosylamine)

Other glycosylamine flavorant compounds include 1-amino-1-deoxymannose (mannosylamine), 1-amino-1-deoxyribose (ribosylamine), 1-amino-1-deoxygalactose (galactosylamine), 1-amino-1-deoxyrhamnose (rhamnosylamine), 1-amino-1-deoxyfucose (fucosylamine), 1-amino-1-deoxyxylose (xylosylamine), 1-amino-1-deoxyarabinose (arabinosylamine), 1-amino-1-deoxylyxose (lyxosylamine), and the like.

The invention glycosylamine compounds in pure form are stable and odorless compounds at ambient temperatures. In addition, the glycosylamine compounds decompose at a relatively low pyrolysis temperature (e.g., 200°–300° C.) to release a high yield of desirable flavor-enhancing components into mainstream smoke.

The volatile pyrolysis components from glycosylamine under cigarette smoking conditions include ammonia, pyrazine and related compounds which have correspondence with desirable flavorant species characteristic of the smoke generated in the combustion of burley tobacco filler. Further, it appears that the glycosylamine additive per se has a direct favorable impact on the flavor and aroma of tobacco smoke under smoking conditions.

Preparation Of Glycosylamines

The synthesis of glycosylamines by interaction of reducing sugars with amines are reported in chemical literature such as the following publications:

Ling et al, J. Chem., Soc., 121, 1682(1922)
Mitts et al, J. Am. Chem. Soc., 66, 483(1944)
Wane et al, J. Am. Chem. Soc., 62, 3314(1940)
Isbell et al, J. Org. Chem., 23, 1309(1958)

In a typical synthesis procedure, a sugar is dissolved in an aqueous alkanol medium at a temperature of 0°–10° C. and ammonia gas is introduced to the medium. The ammoniated solution is maintained under cooling conditions for a period of three days or more. Usually the glycosylamine product crystallizes out of the aqueous medium during the reaction period. The course of the reaction between the sugar and ammonia can be monitored by high performance liquid chromatography (HPLC), ion chromatography or by nuclear magnetic resonance analysis.

If the reaction is conducted at a temperature between about 30°–100° C., the condensation of sugar and ammonia proceeds with rapid formation of the glycosylamine product. In the case of sugars such as rhamnose and mannose, the reaction is completed within about ten minutes.

The rate of the sugar/ammonia reaction at an elevated temperature proceeds rapidly, but it generally is accompanied by a "browning" decomposition side-reaction which can complicate product isolation procedures.

The glycosylamine product in solution can be recovered from the reaction medium by the addition of a water-soluble diluent such as propanol to precipitate the dissolved glycosylamine, or by freeze-drying of the reaction medium, or by other convenient procedures. Purification of a crude glycosylamine product can be accomplished by recrystallization from an aqueous alkanol/ammonia solution.

Ammonia-derived glycosylamines with an unsubstituted amino-group ($-NH_2$) are more stable than glycosylamines in which the amino group is substituted ($-NHR$ or $-NR_2$). If the amino group is an aminoacid structure, then there is a self-catalyzed Amadori Rearrangement, i.e., a conversion of N-glycoside of aldose sugar to an amine derivative of the corresponding ketose, in addition to other side-reactions which occur at room temperature.

Preparation Of Tobacco Compositions

In another embodiment, the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.001 and 5 weight percent, based on composition weight, of a glycosylamine flavorant-release additive corresponding to the formula:

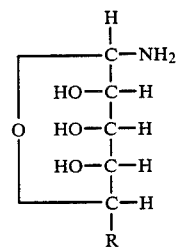

where R is a hydrogen, methyl or methylol substituent.

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.001 and 5 weight percent, based on composition weight, of a glycosylamine flavorant-release additive corresponding to the formula:

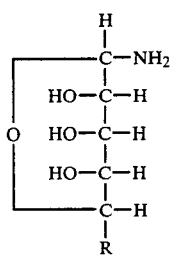

where R is a hydrogen, methyl or methylol substituent; and subjecting the smoking composition to a heat treatment at a temperature between about 75°–200° C.

The heat treatment of the smoking composition is for a period between 0.1–5 hours. The heat treatment of the smoking composition increases the flavor impact of the mainstream smoke under cigarette smoking conditions, as compared to the same smoking composition which has not been heat-treated prior to the smoking phase. The heat treatment of the smoking compositions has the effect of converting the glycosylamine additive to a "browning" complex of flavor-enhancing constituents in the smoking composition, such as pyrazine-containing compounds.

The invention glycosylamine flavorant-release additive can be incorporated into the tobacco in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

It is advantageous to employ directly the reaction medium solution of glycosylamine as synthesized for application to a smoking filler matrix. For example, glucose can be reacted in an aqueous ammonium hydroxide solution at 80°–90° C. for 5–20 minutes, and the resultant solution of glucosylamine can be sprayed into tobacco and/or tobacco substitute smoking filler.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I

This Example illustrates the preparation of a glycosylamine compound which is applicable as a flavorant additive in smoking compositions in accordance with the present invention.

Anhydrous ammonia is bubbled through 100 ml of 95% methanol in a reactor until the solution is saturated with ammonia. To this solution is added 125 grams of glucose in five equal portions while stirring and maintaining the flask at 0° C. Each portion of the glucose is allowed to dissolve with stirring before the next portion is added. The final volume is doubled with 95% methanol, and the solution is maintained at a temperature of about 5° C. for a reaction period of about 20 days. The solid product which has formed is separated by filtration, washed with 100 ml of anhydrous methanol, and dried to provide a crude glucosylamine product. A 64 gram quantity of the solid glucosylamine is dissolved in an equal weight of 10% ammonium hydroxide, and 120 ml of methanol. The solution is diluted with 120 ml of ethanol, and then the resulting solution is cooled at 5° C. to cause the formation of solid glucosylamine in the liquid medium. The glucosylamine is recovered as a white crystalline product.

EXAMPLE II

This Example illustrates the preparation of a present invention smoking composition, and the enhanced mainstream smoke flavor properties it exhibits under cigarette smoking conditions.

An ethanol solution of glucosylamine produced by the procedure of Example I is injected into a cigarette made of bright lamina tobacco to provide a level of 2% by weight. The cigarette is compared to a control cigarette in a smoking test. The glucosylamine-treated cigarette has a distinctive burley-like flavor as compared to the control cigarette.

When a glucosylamine-containing tobacco filler is subjected to a heat treatment at 110° C. for ten minutes and then incorporated in a cigarette, the cigarette has a pleasant toasted flavor under smoking conditions. When the glucosylamine-containing tobacco filler is treated by heating at 110° C. for one hour, under cigarette smoking conditions the resultant mainstream smoke has a chocolate-like character.

EXAMPLE III

This Example illustrates the improved mainstream and sidestream smoke properties of cigarettes in accordance with the present invention.

A.

A 50% aqueous solution of glucosylamine is sprayed onto tobacco filler to a level of 5% by weight of the filler. The filler is utilized to fabricate filter tipped cigarettes designed to deliver 8 mg FTC tar. Smoking of these cigarettes by a panel of experts in comparison to control cigarettes without the glucosylamine demonstrates that the glucosylamine containing cigarettes have a slightly sweet rod aroma with more impact and a slightly nutty pyrazine-like note at the end of the rod than do the control cigarettes.

B.

Employing the procedure of Example II, cigarettes are treated with 5% by weight of rhamnosylamine flavorant additive. Under smoke conditions the treated cigarettes generate smoke exhibiting increased impact with good body and enhanced tobacco character, and the smoke has a slight ginger aroma.

Similar results are obtained when fucosylamine, mannosylamine, ribosylamine, galactosylamine, xylosylamine, lyxosylamine or arabinosylamine is employed as the glycoslyamine flavorant-release additive in smoking tobacco compositions.

What is claimed is:

1. A smoking composition comprising an admixture of (1) combustible filler selected from natural tobacco, reconstituted tobacco and tobacco substitutes, and (2) between about 0.001 and 5 weight percent, based on the total weight of filler, of a glycosylamine flavorant-release additive corresponding to the formula:

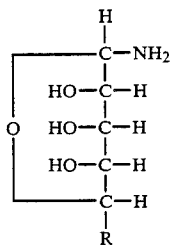

where R is a hydrogen, methyl or methylol substituent.

2. A smoking composition in accordance with claim 1 wherein the tobacco substitutes are selected from pectinaceous cellulosic and other carbohydrate materials.

3. A smoking composition in accordance with claim 1 wherein the additive is 1-amino-1-deoxyglucose.

4. A smoking composition in accordance with claim 1 wherein the additive is 1-amino-1-deoxymannose.

5. A smoking composition in accordance with claim 1 wherein the additive is 1-amino-1-deoxyribose.

6. A smoking composition in accordance with claim 1 wherein the additive is 1-amino-1-deoxygalactose.

7. A smoking composition in accordance with claim 1 wherein the additive is 1-amino-1-deoxyrhamnose.

8. A smoking composition in accordance with claim 1 wherein the additive is 1-amino-1-deoxyfucose.

9. A smoking composition in accordance with claim 1 wherein the additive is 1-amino-1-deoxyxylose.

10. A smoking composition in accordance with claim 1 wherein the additive is 1-amino-1-deoxyarabinose.

11. A smoking composition in accordance with claim 1 wherein the additive is 1-amino-1-deoxylyxose.

12. A method of preparing a smoking composition which is adapted to impart flavor and aroma to mainstream and sidestream smoke under smoking conditions, which method comprises incorporating into natural tobacco, reconstituted tobacco or tobacco substitute between about 0.001 and 5 weight percent, based on composition weight, of a glycosylamine flavorant-release additive corresponding to the formula:

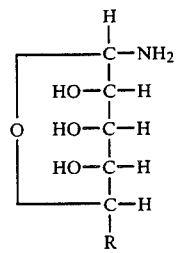

where R is a hydrogen, methyl or methylol substituent.

13. A method of preparing a smoking composition which is adapted to impart flavor and aroma to mainstream and sidestream smoke under smoking conditions, which method comprises incorporating into natural tobacco, reconstituted tobacco or tobacco substitute between about 0.001 and 5 weight percent, based on composition weight, of a glycosylamine flavorant-release additive corresponding to the formula:

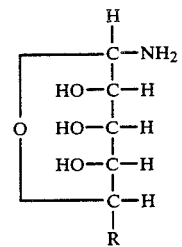

where R is a hydrogen, methyl or methylol substituent; and subjecting the smoking composition to a heat treatment at a temperature between about 75°–200° C.

14. A method in accordance with claim 13 wherein the heat treatment of the smoking composition is for a period between about 0.1–5 hours.

15. A smoking composition which is prepared in accordance with the method of claim 13.

* * * * *